United States Patent
Osborne

(10) Patent No.: US 8,303,627 B2
(45) Date of Patent: Nov. 6, 2012

(54) PATENT FORAMEN OVALE CLOSURE DEVICE AND METHOD

(75) Inventor: Thomas A. Osborne, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1162 days.

(21) Appl. No.: 12/159,829

(22) PCT Filed: Jan. 9, 2007

(86) PCT No.: PCT/US2007/000345
§ 371 (c)(1),
(2), (4) Date: Jul. 1, 2008

(87) PCT Pub. No.: WO2007/081836
PCT Pub. Date: Jul. 19, 2007

(65) Prior Publication Data
US 2008/0306509 A1    Dec. 11, 2008

Related U.S. Application Data

(60) Provisional application No. 60/757,377, filed on Jan. 9, 2006.

(51) Int. Cl.
*A61B 17/068* (2006.01)
(52) U.S. Cl. ........ 606/242; 606/139; 606/142; 606/144; 606/147; 606/190; 606/219
(58) Field of Classification Search .......... 606/139, 606/142, 144, 147, 190, 219
See application file for complete search history.

(56) References Cited

U.S. PATENT DOCUMENTS 6,461,366 B1 * 10/2002 Seguin .................. 606/144
2002/0026208 A1   2/2002 Roe et al. .............. 606/190

FOREIGN PATENT DOCUMENTS

| FR | 2768324 A1 | 3/1999 |
| WO | WO 2005/027753 A | 3/2005 |
| WO | WO 2005/034763 A | 4/2005 |

OTHER PUBLICATIONS

International Search Report dated May 21, 2007, from International Application No. PCT/US2007/000345.

* cited by examiner

*Primary Examiner* — Vy Q Bui
(74) *Attorney, Agent, or Firm* — Brinks Hofer Gilson & Lione

(57) ABSTRACT

A device for closure of a patent foramen ovale. The device includes at least one elongated tissue anchor at the distal end of the device. A distal end portion of the tissue anchor is selectively deployable between a closed position in which the distal end portion of the tissue anchor is capable of penetrating the septum and the flap, and a radially extensible position in which the distal end portion of the tissue anchor is capable of engaging the septum or flap so that the septum and flap may be urged into registry. A deployment member is associated with the tissue anchor for selectively deploying the distal end portion of the tissue anchor between the closed position and the radially extensible position. A closure element is disposed at the distal end of the device. The closure element is engageable with the septum and the flap when the septum and flap are in registry, for maintaining such registry. An actuator is associated with the closure element for selectively engaging the closure element with the septum and flap.

8 Claims, 5 Drawing Sheets

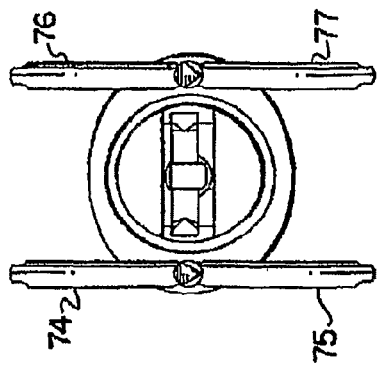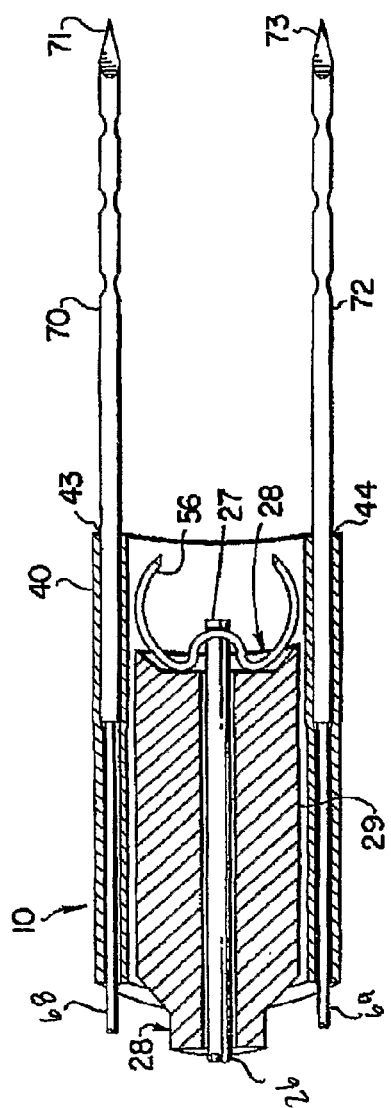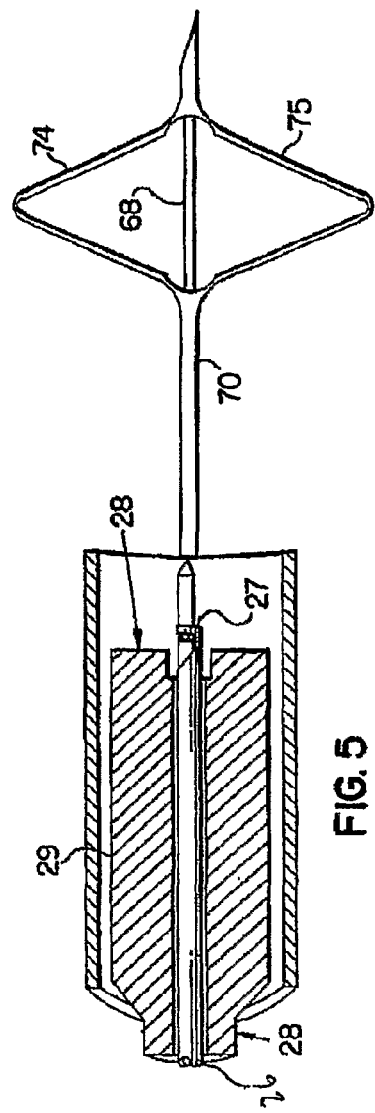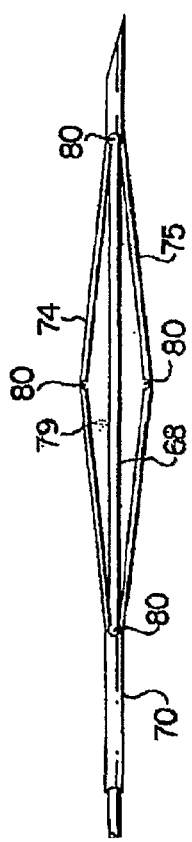

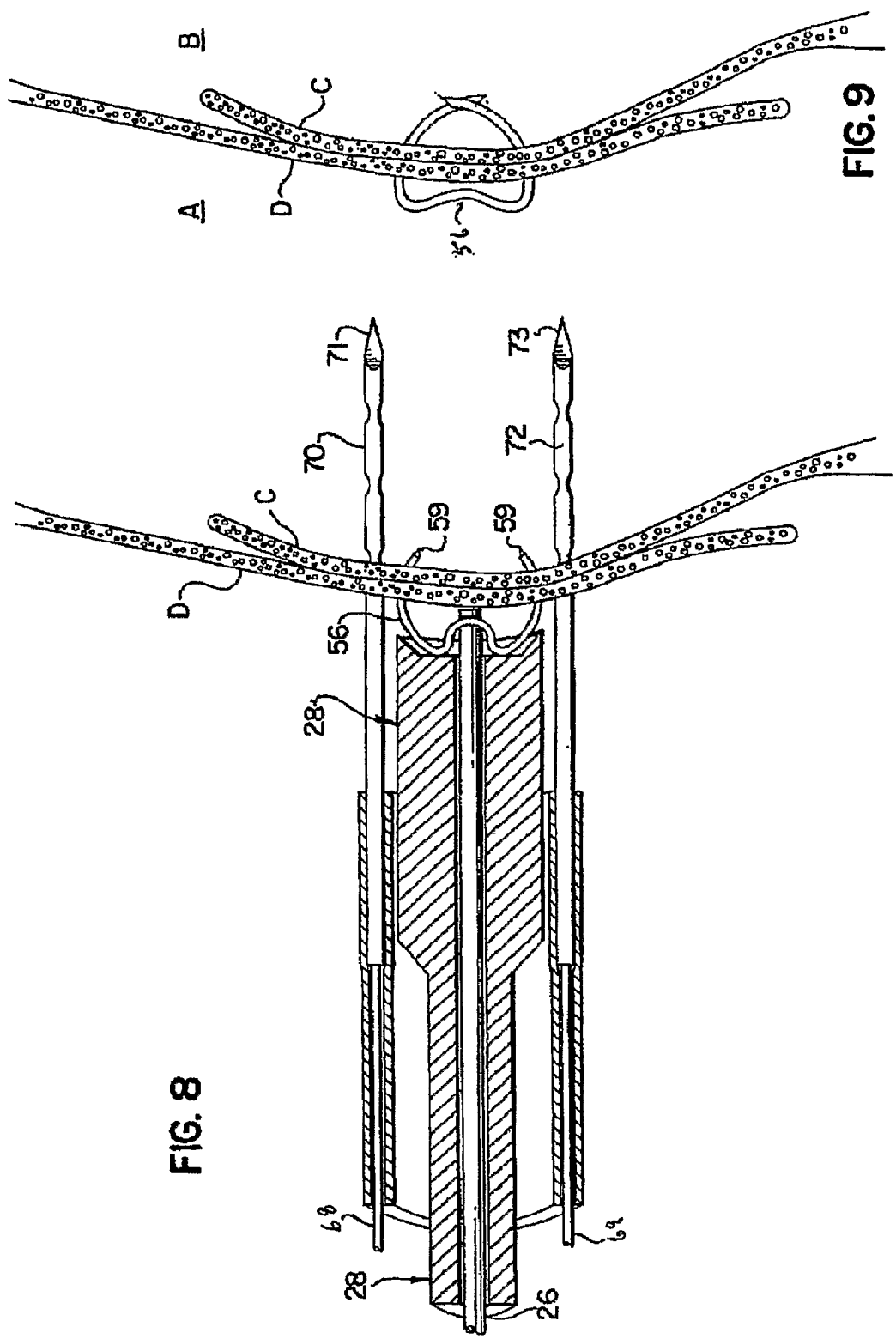

PATENT FORAMEN OVALE CLOSURE DEVICE AND METHOD

TECHNICAL FIELD

The present invention relates to a percutaneously-introduced device for use in the closure of a patent foramen ovale, and to a method for closure of a patent foramen ovale utilizing the percutaneously-introduced device.

BACKGROUND OF THE INVENTION

In the fetal heart, there is a small communication, referred to as the foramen ovale, in the septum between the right and left atria. In the unborn fetus, this communication allows blood to bypass the lungs. Fetal blood is oxygenated by the lungs of the mother. This communication normally closes within the first year after birth, and oxygenation is carried out through the baby's own lungs. Although the remnant of the opening remains in the septum after birth, the remnant normally does not allow passage of blood.

In some cases, however, this opening (the foramen ovale) remains patent and the baby's oxygenated blood is diluted by un-oxygenated venous blood. Babies with this condition often have very little energy, are cyanotic (blue coloration), and do not progress well after birth. In order to repair this defect, the opening can be closed by surgical methods, or by newer percutaneous methods. This condition in newborns is often referred to as an atrial septal defect (ASD).

In recent years, physicians have also discovered that in a large percentage of adults, estimated at about 30%, the foramen ovale has not completely sealed, and remains as a small patent foramen ovale. In these adults, there is still some leakage across the septum through the remnant foramen ovale. Although such leakage is not always problematic, the leakage can be aggravated upon certain types of strain or valsalva. Intermittent leakage of blood through the PFO has been linked to migraine headaches and other maladies. In addition, a PFO is suspected as being a passageway for blood clots. Passage of clots through the opening can lead to a stroke or a transient ischemic attack (TIA).

The leaking, or patent, foramen ovale does not result from the same physiological structure as an ASD. An ASD is normally a definable hole that extends through the septum. Such holes can be occluded by passing known occluder devices through the hole, such that the devices anchor on each side of the septum to form a seal. Current devices that are commonly used for ASD repair include the Amplatzer ASD Occluder, available from AGA Medical, and the Gianturco occluder coils, available from Cook Incorporated.

Unlike the definable hole that forms an ASD, the foramen ovale is a small channel or slot-type structure that is defined by the septum and a flap that covers a part of the ovale. With a PFO, the septum and the flap normally overlap to a certain degree, and are not fused together as in the normal case. As a result, small amounts of blood may leak through a passageway that extends between the septum and the flap.

Currently available ASD repair devices are ill suited for repair of a PFO. As stated, ASD repair devices normally comprise an occluder-type structure that is extended through the septum hole that comprises the defect to seal the opening. However, with a PFO, the openings on each side of the septum are offset, and not in line with each other (i.e., not directly across from each other). The leakage path is under a flap, and through a narrow passageway, rather than a defined hole. Thus, it is not generally sufficient to merely provide a plug for a hole, as in conventional ASD repair.

Open heart surgical methods have been used for PFO repair. Such methods normally entail breaking open the chest cavity, and cutting into the heart muscle. The flap is then sutured or otherwise attached to the septum, in a manner such that the passageway is closed. Although generally effective for closing the PFO, such methods are intrusive, costly, and require an extended recovery period for the patient.

Recently, percutaneous methods have been developed for repair of a PFO. These methods involve utilizing conventional percutaneous entry techniques, such as the Seldinger technique, and passing a catheter through a vessel into the right atrium of the heart. One device used in such methods, known as the Amplatzer PFO Occluder, comprises a plug-like device formed of a self-expanding wire-mesh with double discs. This device contains inner polyester fabric patches that, along with the wire mesh, are intended to cause the formation and accumulation of a blood clot. The resulting blood clot is positioned to block the opening. Devices of this type are complex mechanically, require a high level of skill to insert properly, and result in the formation of a clot which actually forms the seal.

There exists a need for a device for providing effective closure of a patent foramen ovale, which device is suitable for percutaneous entry, is less complex mechanically and operationally when compared to prior art devices, and can be utilized for patent foramen ovale closure with minimal trauma to the patient.

SUMMARY OF THE INVENTION

The present invention addresses the shortcomings of the prior art. In one form thereof, the present invention comprises a device for closure of a patent foramen ovale. The device comprises at least one elongated tissue anchor extending between the proximal end and the distal end of the device. A distal end portion of the tissue anchor is capable of penetrating the septum and the flap, which tissue anchor distal end portion is selectively deployable between a closed position and a radially extensible position. The tissue anchor distal end portion of is axially movable relative to the septum and flap such that upon radial extension of the extensible portion the septum and flap may be urged into registry, at which time the foramen ovale is substantially closed to passage of fluids therethrough. A deployment member is engaged with the tissue anchor for selectively deploying the radially extensible portion of the tissue anchor between the closed position and the radially extensible position. A closure element, such as a staple, is disposed at the distal end of the device. The closure element has an open position wherein an end portion of the closure element is capable of penetrating the septum and flap when the septum and flap are in registry, and a closed position for maintaining the septum and flap in registry. An actuator is operatively engaged with the closure element for selectively manipulating the closure element from the open position to the closed position.

The present invention, in another form, comprises a method for patent foramen ovale closure. A device comprising a tissue anchor and a closure element is provided for closure of the patent foramen ovale. The tissue anchor extends to a distal end of the device, and has a distal end portion selectively deployable between a closed position and a radially extensible position. The closure element is provided for sealing the flap and the septum of the foramen ovale. The device is percutaneously introduced into an atrium of the heart of a patient, and aligned in a manner such that the distal end portion of the tissue anchor is spaced from one of the septum and the flap at the patent foramen ovale. The septum and flap are then penetrated at the patent foramen ovale with the distal end portion of the tissue anchor. The distal end portion of the tissue anchor is deployed to the radially extensible position, and aligned with the septum and flap in a manner such that the septum and flap are in registry. The aligned septum and flap are then penetrated with the closure element, and the closure element is actuated to maintain the septum and flap in registry, thereby sealing the foramen ovale.

The present invention, in still another form, comprises a device for closure of a patent foramen ovale. The device includes at least one elongated tissue anchor at the distal end of the device. A distal end portion of the tissue anchor is selectively deployable between a closed position in which the distal end portion of the tissue anchor is capable of penetrating the septum and the flap, and a radially extensible position in which the distal end portion of the tissue anchor is capable of engaging the septum or flap so that the septum and flap may be urged into registry. A deployment device is associated with the tissue anchor for selectively deploying the distal end portion of the tissue anchor between the closed position and the radially extensible position. A closure element is disposed at the distal end of the device. The closure element is engageable with the septum and the flap when the septum and flap are in registry for maintaining the septum and flap in registry. An actuator is associated with the closure element for selectively engaging the closure element with the septum and flap.

BRIEF DESCRIPTION OF THE DRAWING

FIG. 4 is a sectional side view of the distal portion of the PFO closure device;

FIG. 5 is a sectional side view rotated 90 degrees from the view of FIG. 4, with the radially extensible portions of the device in an open position;

FIG. 6 is a distal end view taken from the perspective of FIG. 5;

FIG. 7 is a side view of the distal portion of the PFO closure device, showing the extensible positions in a substantially closed position;

FIG. 8 is a sectional side view of the distal portion of the PFO closure device, showing the tissue anchors and the ends of the staple penetrating the septum and flap;

FIG. 9 is a side view similar to the view of FIG. 8, showing the staple closed around the septum and flap, closing the PFO;

DETAILED DESCRIPTION

Figure 1:
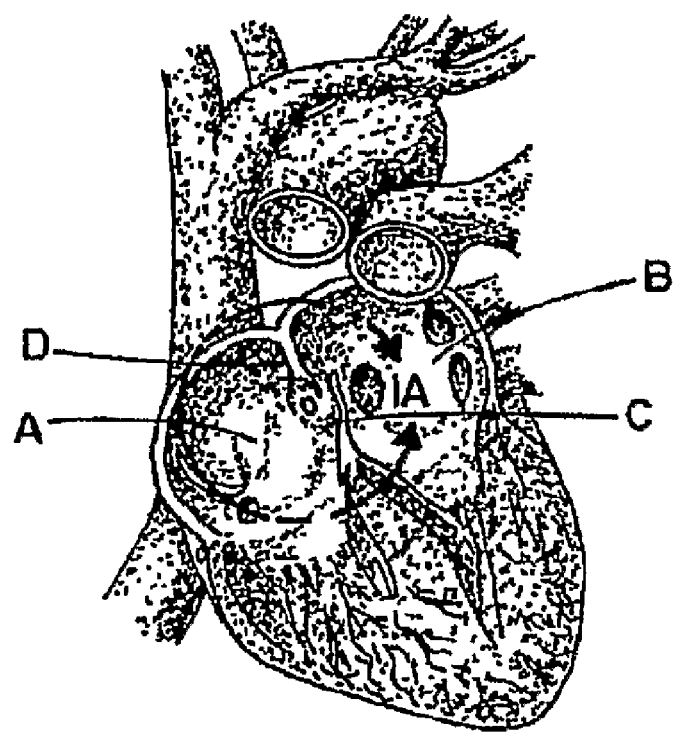
FIG. 1 is an illustration of the internal portions of the heart.

For purposes of promoting an understanding of the present invention, reference will now be made to the embodiments illustrated in the drawings, and specific language will be used to describe the same. It is nevertheless to be understood that no limitation of the scope of the invention is thereby intended. The figures are not all drawn to the same scale to avoid obscuring the details of the finer structures. The following detailed description of the preferred embodiments will make clear the preferred arrangement, size relationships and manner of using the components shown herein.

The present invention relates to a device and method for patent foramen closure. In the following discussion, the terms "proximal" and "distal" will be used to describe the opposing axial ends of the device used in the inventive method, as well as the axial ends of various component features of the device. The term "proximal" is used in its conventional sense to refer to the end of a device (or component) that is closest to the operator during use of the device. The term "distal" is used in its conventional sense to refer to the end of a device (or component) that is initially inserted into the patient, or that is closest to the patient.

Figure 1A:
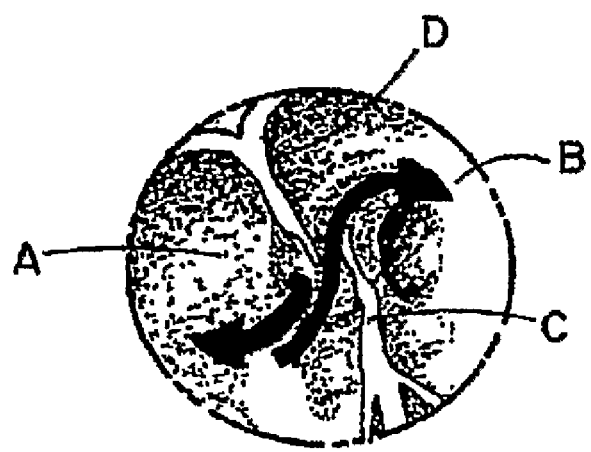
FIG. 1A is an enlarged view of a portion of the heart shown in FIG. 1, illustrating the location of a patent foramen ovale.

FIG. 1 is an illustration of the internal portions of the heart, showing the right atrium A, left atrium B, septum C that separates the right and left atria, and flap D that extends along a portion of the septum C. Septum C and flap D define a channel (shown by the arrows in FIG. 1A) therebetween that comprises the patent foramen ovate. The presence of the PFO undesirably establishes a communication between the atria. This communication allows blood to leak between the chambers, which leakage can result in the migration of unoxygenated blood from the left atrium to mix with the oxygenated blood in the right atrium. Such leakage has been linked to migraine headaches and other maladies described above, such as a stroke or a transient ischemic attack (TIA).

FIGS. 2-9 illustrate a device 10 for closure of a PFO, according to one embodiment of the present invention. Device 10 may be used to apply a closure element, such as a staple, for binding septum C and flap D in a manner such that the patent foramen ovale is at least substantially closed, as further described herein.

Figure 2:
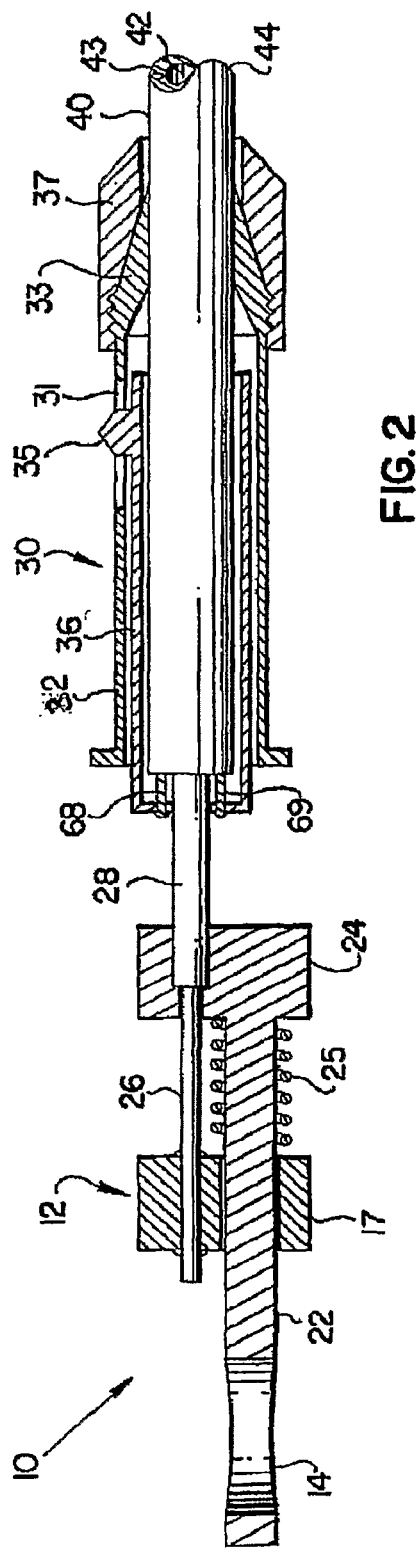
FIG. 2 is a side view, partially in section, of the proximal portion of a PFO closure device according to one embodiment of the present invention.
Figure 3:
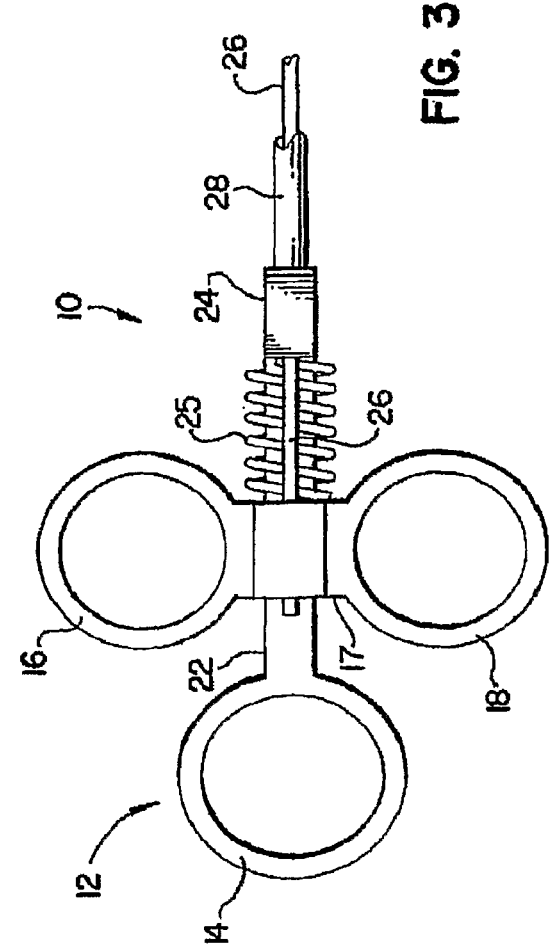
FIG. 3 illustrates a side view, rotated 90 degrees from the view of FIG. 2, of the proximal portion of a PFO closure device.

A proximal end of device 10 is illustrated in FIGS. 2 and 3. As illustrated, device 10 comprises a handle 12, such as the three ring handle shown in the figure. In the embodiment shown, three ring handle 12 includes a proximal ring 14 at the proximal end of the device, and opposing lateral rings 16, 18 positioned slightly distal to ring 14 along the length of device 10. Lateral rings 16, 18 are provided for deployment of the staple for closure of the PFO, in a manner to be described. Handles for medical devices are well known in the art, and a skilled artisan may readily modify handle 12 for a particular purpose when armed with the teachings of the present invention.

Proximal ring 14 is joined via extender 22 to shoulder element 24. In the preferred embodiment shown, shoulder element 24 is positioned for compressing a bias member, such as helical spring 25, for actuation of the staple. Rings 16, 18 are joined by joinder element 17. Joinder element 17 fixedly receives the proximal end of an actuator wire 26 for the staple, in a manner such that proximal or distal movement of rings 16, 18 pulls actuator wire 26 in a like direction. Actuator wire 26 is slidably received in staple carrier 28 for relative movement therewith. Staple carrier 28 extends through a tissue anchor carrier 40 substantially to the distal end of device 10. See, e.g., FIG. 4.

As shown in FIG. 2, device 10 also includes a sleeve handle 30 for operation of tissue anchors 70, 72 (FIG. 4). In the embodiment shown, sleeve handle 30 includes coaxial sleeves 32, 36. Outer sleeve 32 has a tapered distal end 33 affixed to tissue anchor carrier 40. Tissue anchor carrier 40 is an elongated shaft extending substantially from the proximal end of device 10, as shown in FIG. 2, to the distal end of the device, as shown, e.g., in FIG. 4. Tissue anchor carrier 40 is sized and shaped to carry tissue anchors 70, 72, in a manner to be described. Outer sleeve distal end 33 may be affixed to tissue anchor carrier 40 by any conventional means, such as by aligning chuck 37 over distal end 33 and fitting chuck 37 to the exterior of sleeve handle 30. Alternatively, an adhesive or other suitable joinder mechanism may be substituted for chuck 37.

A pair of tissue anchor deployment wires 68, 69 are provided for control of tissue anchors 70, 72. The proximal end of tissue anchor deployment wires 68, 69 are affixed by any suitable means, such as brazing, welding or soldering, to the proximal end of coaxial inner sleeve 36, and are movable therewith. In the embodiment shown, tissue anchor deployment wires 68, 69 extend through respective tissue anchors 70, 72. This is best shown in FIG. 4. Coaxial inner sleeve 36, as well as the affixed deployment wires 68, 69, are axially slidable relative to outer sleeve 32, to selectively push or pull tissue anchor deployment wires 68, 69 for activating the extensible portions of tissue anchors 70, 72, in a manner to be described herein. In the embodiment shown, inner sleeve 36 is slidable by selectively urging, or sliding, deployment member 35 in a proximal or distal direction. As illustrated, deployment member 35 comprises a finger-accessible member that extends through an opening 31 in a wall of outer sleeve 32. Those skilled in the art will appreciate that other means for effecting relative movement between the sleeves may be substituted for the deployment member shown in the figures.

FIGS. 4-7 illustrate various aspects of the distal end of closure device 10. Tissue anchor carrier 40 comprises an elongated multi-lumen tube having a major central lumen 42 sized for axial movement of staple carrier 28 therethrough, and smaller parallel lumens 43, 44 sized for axial movement of tissue anchors 70, 72. For ease of use, staple carrier 28 preferably has a smaller diameter main body portion, and a larger diameter distal end 29 (FIGS. 4, 5). Providing the smaller diameter main body portion enhances the flexibility of the staple carrier and the main body portion of the device.

Figure 11:
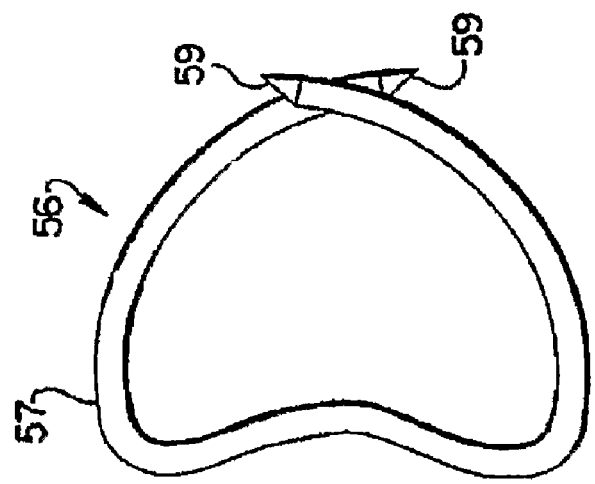
FIG. 11 is a side view of the staple of FIG. 10 in a closed position.
Figure 10:
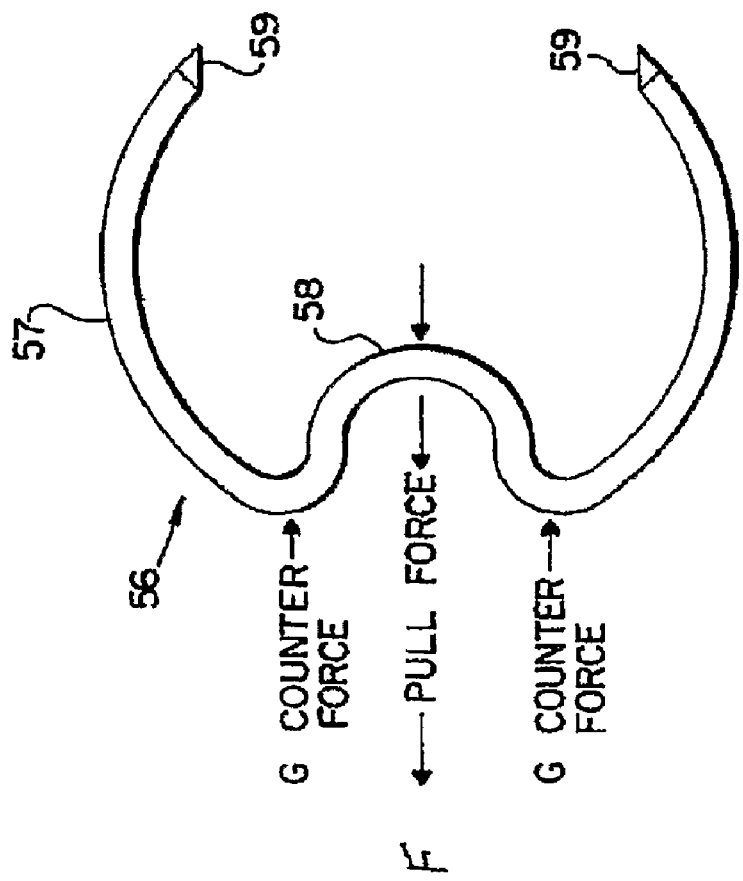
FIG. 10 is a side view of a staple for use in the closure device, wherein the staple is shown in an open position.

A closure element, such as staple 56, is provided at the distal end of staple carrier 28. Actuator wire 26 includes a hook mechanism 27 or like device for holding staple 56 in staple carrier 28. Staple 56 is best shown in FIGS. 10 and 11. In the embodiment shown, staple 56 comprises a generally C-shaped body 57 having an inwardly directed curve 58 positioned substantially at the midpoint of the staple body 57. Preferably, the ends 59 of staple 56 are sharpened to facilitate passage through septum C and flap D. During use of device 10, curve 58 is substantially flattened, as shown in FIG. 11. At this time, respective ends 59 of staple 56 approach, and eventually pass, each other, thereby closing the staple in well-known fashion.

Tissue anchors 70, 72 comprise thinwall needle tubes, preferably formed of a metal or metal alloy, such as stainless steel. Generally parallel elongated slots 79 are formed at the distal end of each of tissue anchors 70, 72, as shown in FIG. 7, and are positioned at opposite sides of the anchor tube. Slots 79 define respective radially extensible portions 74, 75 and 76, 77 of the tissue anchors. Preferably, a small radius 80 is formed at each end of slot 79, and at the midpoint of the slot. (FIG. 7) Providing radii 80 enables the radially extensible portions 74, 75 and 76, 77 (described below) to act in the nature of a hinge. Distal ends 71, 73 of anchors 70, 72 are sharpened in conventional fashion to facilitate passage through septum C and flap D. Deployment wires 68, 69 extend through the respective inner passageways of tissue anchors 70, 72, and are affixed to the tissue anchors, distal of the radially extensible portions, by conventional means, such as soldering, welding, or brazing.

In the embodiment shown, tissue anchor 70 includes respective radially extensible portions 74, 75, and tissue anchor 72 includes respective radially extensible portions 76, 77. As indicated in the figures, the respective extensible portions radially project to form a generally "V"-shape. Those skilled in the art will appreciate that the design shown is exemplary only, and that each tissue anchor need not necessarily have two radially extensible portions. Similarly, the radially extensible portions need not necessarily have a V-shaped configuration. Rather, other radially extensible configurations may be substituted for the V-shape as illustrated herein.

Use of the inventive device in closing a PFO will now be described. Initially, entry may be made into a suitable vessel, such as the femoral artery, by conventional means, such as the well-known Seldinger percutaneous entry technique. In this technique, a puncture is made by injecting a needle into the vessel. A wire guide is then inserted through a bore in the needle into the vessel, and the needle is thereafter withdrawn. The wire guide is threaded into the right atrium of the heart, and a guide catheter is threaded over the wire guide into the atrium. If desired, the guide catheter can be provided with a general purpose curve to aid in directing the device to the PFO. As another alternative, the guide catheter can be provided with a deflectable tip to provide enhanced control in directing the distal end of the catheter. Typically, the guide catheter has a length of about 80-100 cm. Following proper positioning of the guide catheter, the wire guide may be removed.

Utilizing a suitable imaging technique, such as x-ray fluoroscopy, device 10 is then threaded through the guide catheter in the right atrium until the distal end of the device is generally adjacent the PFO, and more specifically, generally adjacent flap D. The device is then further advanced in the distal direction until sharpened ends 71, 73 of respective tissue anchors 70, 72 pierce flap D and septum C. At this time, the respective radially extensible portions 74, 75 of tissue anchor 70, and radially extensible portions 76, 77 of tissue anchor 72 are on the side of septum C and flap D opposite that of the remainder of device 10, as shown in FIG. 8.

Respective radially extensible portions 74, 75 and 76, 77 are then deployed, or opened, to the configuration shown in FIG. 5 by sliding deployment member 35 in the proximal direction. Proximal movement of deployment member 35 urges inner sleeve 36, and therefore the affixed deployment wires 68, 69, in the proximal direction. Proximal movement of the deployment wires extends respective portions 74, 75 and 76, 77 to form the V-shape, as shown in FIGS. 5 and 7. Device 10 may then be retracted slightly in the proximal direction, such that the radially extensible portions urge septum C and flap D into registry, or in other words, into a position such that they substantially abut each other. Handle 12 may then be advanced in the distal direction, such that staple ends 59 pierce the flap D and septum C, as shown in FIG. 8.

Rings 16, 18 are then withdrawn in the proximal direction, thereby driving proximal movement of the affixed actuation wire 26. Staple 56 is thereby withdrawn in the proximal direction, until it abuts the distal end of staple carrier 28. Contact of staple 56 with staple carrier 28 results in the creation of a pull force F on staple midpoint 58, and a counterforce G at each adjacent side of midpoint 58. This is shown in FIG. 10. As a result, staple midpoint 58 is substantially flattened, as shown in FIG. 11. As the curve flattens, sharp staple ends 59 advance toward each other, thereby eventually closing the staple, and the PFO, as shown in FIG. 9.

Following closure of the PFO as described, slidable deployment member 35 is urged in the distal direction, thereby returning the radially extensible portions to their non-deployed position. Tissue anchors 70, 72 are then withdrawn through the joined septum and flap, and the entire device may be withdrawn through the guide catheter.

Although the method discussed herein describes the application of a single closure staple, the method of operation may be repeated to apply additional staples or closure elements in the event that at abnormally large PFO is present, or in the event that additional closure is otherwise desired. Application and use of closure elements, such as staples, to secure together and maintain a desired alignment of separate tissue segments is well known in the medical arts.

As a result of the registration of the septum and flap via the closure element as described, the PFO is immediately sealed. Over time, the tissue of the flap will become incorporated into the septum. The use of a small closure element, such as a staple, enables the closure element to endothelialize and become a permanent part of the septum.

Although a preferred embodiment of the inventive method has been described, those skilled in the art will appreciate that modifications can be made to the preferred embodiment described herein within the spirit and scope of the invention. For example, the inventive method has been described as making the initial entry into the femoral vein. Although this vein is commonly used to provide a pathway for access to the heart for percutaneous entry techniques, other suitable veins and arteries may likewise be utilized for access to an atrium of the heart. In addition, although initial access into the artery or vein has been described by utilizing the well-known Seldinger technique, other known percutaneous entry techniques may be substituted. Similarly, in the method as described, the guide catheter is introduced over a wire guide. Although use of a wire guide is preferred, such use is not required. Those skilled in the art are aware that other suitable devices and techniques, such as flow directed catheters, may be utilized in place of the use of the catheter/wire guide combination described herein.

The preferred embodiment utilizes staples to close the PFO. Those skilled in the art will appreciate that other closing elements known for closing or otherwise occluding an opening between tissue segments may be substituted for the preferred mechanism described. One common alternative is to join the septum and flap with sutures. The use of sutures in the medical arts is well known, and further description of this technique is not necessary. Similarly, the septum and flap can be joined by other known joinder means, such as glue and other biologically-appropriate adhesives.

Although the present invention has been described with reference to its preferred use as a device and method for closure of a PFO, the invention is not so limited. Rather, the inventive device and method can be extended to the closure of other small channels or passageways encountered within the body of a patient.

Those skilled in the art will appreciate that the length of the device may be varied depending upon factors such as the entry site for the device, the size of the patient, the particular opening to be closed, etc. For use in closing a patent foramen ovale via entrance through the femoral artery of a typical adult patient, a length of about 125 to 150 cm will generally be sufficient. Similarly, the diameter of the device may be varied for to take account for well-known variables, such as those described above. Typically, a diameter of 8 to 12 French, and more typically 8 to 10 French will be sufficient.

While these features have been disclosed in connection with the illustrated preferred embodiment, other embodiments of the invention will be apparent to those skilled in the art that come within the spirit of the invention as defined in the following claims.

The invention claimed is:

1. A device for closure of a patent foramen ovale, said patent foramen ovale extending between a septum and a flap in the interior space of the heart of a patient, said device having a proximal end and a distal end, comprising:
   a pair of elongated tissue anchors extending between said proximal end and said distal end of said device, each tissue anchor having an axial bore therethrough and having a distal end portion capable of penetrating said septum and said flap, each of said distal end portions being selectively deployable between a closed position and a radially extensible position, each of said distal end portions being axially movable relative to said septum and flap such that upon radial extension of said extensible portion said septum and flap may be urged into registry, wherein said foramen ovale is substantially closed to passage of fluids therethrough;
   a deployment member engaged with each of said tissue anchors for selectively deploying the radially extensible portion of said tissue anchor between said closed position and said radially extensible position;
   a carrier for said tissue anchors, said carrier comprising an elongated shaft extending substantially to the distal end of said device, said carrier comprising a larger diameter lumen extending substantially through an axial center of said carrier, said carrier further comprising a respective smaller diameter lumen for each of said tissue anchors, said smaller diameter lumens extending axially through a wall surface of said carrier, wherein said distal end portions of said respective tissue anchors extend distal of said carrier;
   a sleeve handle for receiving a proximal end of said carrier, said sleeve handle comprising an outer sleeve and an inner sleeve, said carrier received in a bore in said inner sleeve;
   a deployment wire extending through each of said tissue anchor axial bores, a proximal end of each deployment wire engaged with said inner sleeve and movable therewith, and a distal end of each said deployment wire affixed to a respective tissue anchor distal of said radially extensible portion;
   a closure element disposed at said distal end of said device, said closure element having an open position wherein an end portion of said closure element is capable of penetrating said septum and said flap when said septum and flap are in registry, and a closed position for maintaining said septum and flap in registry; and
   an actuating member engaged with said closure element for selectively manipulating said closure element from said open position to said closed position.

2. The device of claim 1, wherein each said tissue anchor includes two radially extensible portions, each of said radially extensible portions capable of extending in a radially opposite direction when compared to the other of said radially extensible portion.

3. The device of claim 1, wherein each of said tissue anchor distal portions includes a hinged element, each of said hinged elements disposed axially at said closed position and disposed radially at said radially extensible position.

4. The device of claim 1, further comprising a handle at said proximal end of said device, a portion of said handle being axially movable in a proximal direction along said device, wherein said actuating member comprises a wire extending from said axially movable handle portion to said closure element at said distal end of said device.

5. The device of claim 4, wherein said closure element comprises a staple, said staple having at least one end configured for penetrating said septum and said flap when said staple is in said open position.

6. The device of claim 5, further comprising a carrier for said staple, said staple carrier sized to be received in said larger diameter lumen, and configured for maintaining said staple in said open position at a distal end of said carrier.

7. The device of claim 6, wherein said staple carrier has a bore therethrough, said actuating member being received in said bore, said actuating member being proximally movable relative to a distal end of said staple carrier for manipulating said staple to said closed position.

8. The device of claim 1, wherein a portion of said outer sleeve is fixedly engaged with said tissue anchor carrier for relative movement therewith, said outer sleeve including an opening in a wall thereof, and said deployment member comprising a radial projection on a wall of said inner member and extending through said opening, said deployment member being movable for selectively deploying said distal end portion of said tissue anchor between said closed position and said radially extensible position.

* * * * *